(12) United States Patent
Raimondi et al.

(10) Patent No.: US 11,273,023 B2
(45) Date of Patent: Mar. 15, 2022

(54) IMPLANTABLE MEDICAL DEVICE

(71) Applicants: POLITECNICO DI MILANO, Milan (IT); UNIVERSITA' DEGLI STUDI DI MILANO-BICOCCA, Milan (IT); CONSIGLIO NAZIONALE DELLE RICERCHE, Rome (IT)

(72) Inventors: Manuela Teresa Raimondi, Milan (IT); Giulio Cerullo, Milan (IT); Claudio Conci, Saronno (IT); Tommaso Zandrini, Milan (IT); Roberto Osellame, Milan (IT); Giuseppe Chirico, Saronno (IT)

(73) Assignees: POLITECNICO DI MILANO, Milan (IT); UNIVERSITA' DEGLI STUDI DI MILANO-BICOCCA, Milan (IT); CONSIGLIO NAZIONALE DELLE RICERCHE, Rome (IT)

( * ) Notice: Subject to any disclaimer, the term of this patent is extended or adjusted under 35 U.S.C. 154(b) by 88 days.

(21) Appl. No.: 16/955,851

(22) PCT Filed: Dec. 18, 2018

(86) PCT No.: PCT/IB2018/060222
§ 371 (c)(1),
(2) Date: Jun. 19, 2020

(87) PCT Pub. No.: WO2019/123227
PCT Pub. Date: Jun. 27, 2019

(65) Prior Publication Data
US 2020/0337824 A1    Oct. 29, 2020

(30) Foreign Application Priority Data

Dec. 21, 2017 (IT) .................. 102017000147857

(51) Int. Cl.
*A61F 2/00* (2006.01)
*A61B 5/00* (2006.01)

(52) U.S. Cl.
CPC .......... *A61F 2/0077* (2013.01); *A61B 5/0071* (2013.01); *A61F 2002/0081* (2013.01);
(Continued)

(58) Field of Classification Search
CPC .............. A61F 2/007; A61F 2002/0081; A61F 2230/0067; A61F 2240/008;
(Continued)

(56) References Cited

U.S. PATENT DOCUMENTS

2011/0195496 A1    8/2011    Muraguchi et al.

FOREIGN PATENT DOCUMENTS

WO    2017037108 A1    3/2017

OTHER PUBLICATIONS

Manuela T. Raimondi, et al.; "Three-dimensional structural niches engineered via two-photon laser polymerization promote stem cell homing"; Acta Biomateriala; Netherlands, Aug. 21, 2012.

*Primary Examiner* — Dinah Baria
(74) *Attorney, Agent, or Firm* — Dickinson Wright PLLC; Andrew D. Dorisio

(57) ABSTRACT

An implantable medical device obtained by means of two-photon laser polymerisation of a resin to form a three-dimensional matrix, wherein: said three-dimensional matrix comprises a number of levels distributed in height; and said three-dimensional matrix comprises reference means designed to uniquely identify the height of each level from a pre-set reference, by means of a multi-photon fluorescence-excitation microscope; said implantable medical device being characterised in that said reference means comprise a solid having a cross section that varies with height.

10 Claims, 3 Drawing Sheets

(52) U.S. Cl.
CPC . *A61F 2230/0067* (2013.01); *A61F 2240/008* (2013.01); *A61F 2250/0037* (2013.01); *A61F 2250/0081* (2013.01); *A61F 2250/0096* (2013.01)

(58) Field of Classification Search
CPC ...... A61F 2250/0037; A61F 2250/0096; A61F 2250/0081; A61B 5/0071
See application file for complete search history.

*a*

*b*

IMPLANTABLE MEDICAL DEVICE

FIELD OF THE INVENTION

The present invention refers to an implantable medical device and to a method for enabling identification of a level referenced to a reference level in an implantable medical device.

BACKGROUND

Approval for clinical use of a biomaterial, understood as a natural or synthetic material that is suitable for implantation in living organisms, is always the last part of a complex and extremely regulated procedure, the purpose of which is to demonstrate the biocompatibility of the material. In fact, medical devices proposed for worldwide distribution must necessarily follow international standards, which are a fundamental element in harmonised regulatory processes in order to ensure minimum standards of safety, quality, and performance of such medical devices.

New biomaterials must be tested in vivo, following upon a procedure of subcutaneous implantation.

In particular, approval of implantable medical devices, such as biomaterials, is regulated by the ISO 10993 set of standards.

According to these standards, an extremely large number of guinea pigs have to be sacrificed along a series of multiple timepoints, purposely established in order to quantify formation of the fibrotic capsule, inflammation, presence of polymorphonuclear cells, giant cells (Langhans cells), plasma cells, neo-vascularisation, fibrosis and/or degradation of the implanted material. This procedure for validation and approval of a biomaterial of a new type entails, as a consequence, very high costs and involves a series of operations that may well be deemed unethical.

Precisely in order to optimise this procedure, and to reduce the corresponding costs, several attempts have been made to introduce intravital microscopy, which enables in-vivo observation of the material implanted at a sub-cutaneous level. The term "intravital microscopy" refers to a series of experimental approaches mainly used in the observation of tumours, where the microcirculation of organs and tissues is rendered accessible to direct observation and is monitored thanks to techniques of optical microscopy.

Intravital microscopy can be used for quantifying various factors, amongst which the rate of sub-cutaneous neo-vascularisation and of reaction to a foreign body. This may be observed in terms of analysis at a cellular level, simply thanks to the observation of an individual animal during different timepoints, without the need to suppress or subject the recipient to surgical operations of various nature, once the pre-set time window has been reached.

For this purpose, over the years specific observation chambers (commonly known as "window chambers") have been used, which are implanted in the recipient animal following upon extremely invasive surgical operations. Such window chambers were qualified as extremely versatile and effective in all their applications; however, no account had been taken of the price to pay on the part of the recipient. The recipient, in fact, had to be subjected to repeated surgical operations, which were extremely invasive and ethically questionable from many points of view and which brought the recipient to a state of full-blown suffering and stress for the entire duration of the implantation. In addition, such chambers were able to provide just a limited temporal duration and did not allow re-positioning at a micrometric level of the field of observation at each time window sequentially analysed. All these reasons have rendered window chambers insufficient to meet the directives of ISO 10993-6 in terms of quantification of the response due to the implanted foreign body, thus not excluding use of histological analyses and consequent sacrifice of the animal.

To overcome this limit, scaffolds of a micrometric size were positioned both within the window chamber and in portions without any percutaneous access in order to reduce the surface area of observation, to the advantage of the observable volume. Such scaffolds did not, however, allow easy identification of the spatial region observed at successive intervals.

SUMMARY

The aim of the present invention is to provide an implantable medical device that will not be invasive for the recipient.

Another aim is to provide an implantable medical device that will enable unique identification of a spatial region observed.

According to the present invention, the above aims and others still are achieved by an implantable medical device provided by means of two-photon laser polymerisation of a resin to form a three-dimensional matrix, wherein: said three-dimensional matrix comprises a number of levels distributed in height; and said three-dimensional matrix comprises reference means designed to uniquely identify the height of each level from a pre-set reference, using a multiphoton fluorescence-excitation microscope; said implantable medical device being characterised in that said reference means comprise a solid having a cross section that varies with height.

The above aims are moreover achieved by a method for enabling identification in an implantable medical device of a height referenced to a reference system using a multiphoton fluorescence-excitation microscope, comprising the step of associating with said device reference means designed to uniquely identify the height of each level from a pre-set reference, via a dependence between a measurable size of said reference means and the height of the level.

Further characteristics of the invention are described in the dependent claims.

The advantages of the present solution over the solutions according to the prior art are multiple.

The solution proposed consists of a miniaturised device dedicated to intravital optical microscopy centred on the observation of cell dynamics.

The device is constituted by a micro-geometry with controlled porosity that functions as guide for growth of newly formed tissue. This micro-geometry is obtained by means of two-photon photopolymerisation in a non-cytotoxic photosensitive material with appropriate photo-initiator. Said material, once developed, is in turn luminescent under infrared excitation by two-photon absorption.

The device thus obtained will hence preferably be coupled to a newly manufactured biomaterial and will be implanted in an animal according to current standards. The implantation and observation site will be without any percutaneous access, unlike the window chambers commonly used. The device will be colonised by the tissue of the recipient, and the micro-geometry will guide said re-growth in situ, enabling neo-vascularisation of the portion. The device will moreover enable microscopy observations repeated over time in one and the same spatial position. This technology hence for the first time enables objective, continued, and prolonged quantitative analyses of the inflammatory response to the implant, by means of non-invasive real-time longitudinal observations. Thanks to this solution it will no longer be necessary to sacrifice the animal subjected to testing at each observation timepoint.

The advantages of the device are of both an economic and an ethical nature.

Considering the economic aspect, the device will enable reduction of development costs linked to testing of biomaterials/drugs, as well as reduction of the number of animals used for the experiment.

A large number of animals implies large specific structures (animal rooms), dedicated staff, and high management costs.

From an ethical standpoint, the number of animals sacrificed is consequently reduced, and likewise the suffering linked to the implantation of standard window chambers is reduced. The total absence of a percutaneous access, afforded by the device, completely eliminates the need for long, complex, and highly ethically questionable surgical operations on the recipient.

BRIEF DESCRIPTION OF THE DRAWING FIGURES

The characteristics and advantages of the present invention will emerge clearly from the ensuing detailed description of a practical embodiment thereof, which is illustrated by way of non-limiting example in the attached drawings, wherein:

FIG. 1a shows the means for observation and acquisition of the image, FIG. 1b shows an implanted device, along with an enlargement thereof, and FIG. 1c shows a detail of a device, with schematic representation of cellular re-growth;

DETAILED DESCRIPTION

Figure 1:
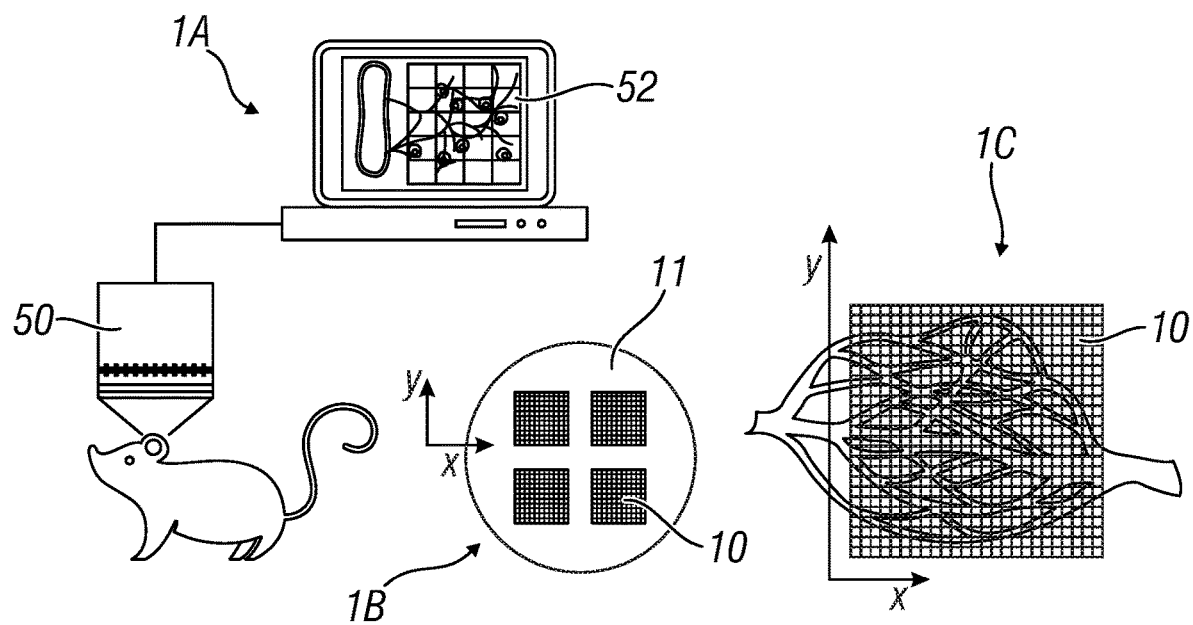
FIG. 1 is a schematic overall illustration of the implantable medical device and of the equipment for viewing it, according to the present invention, where
Figure 2:
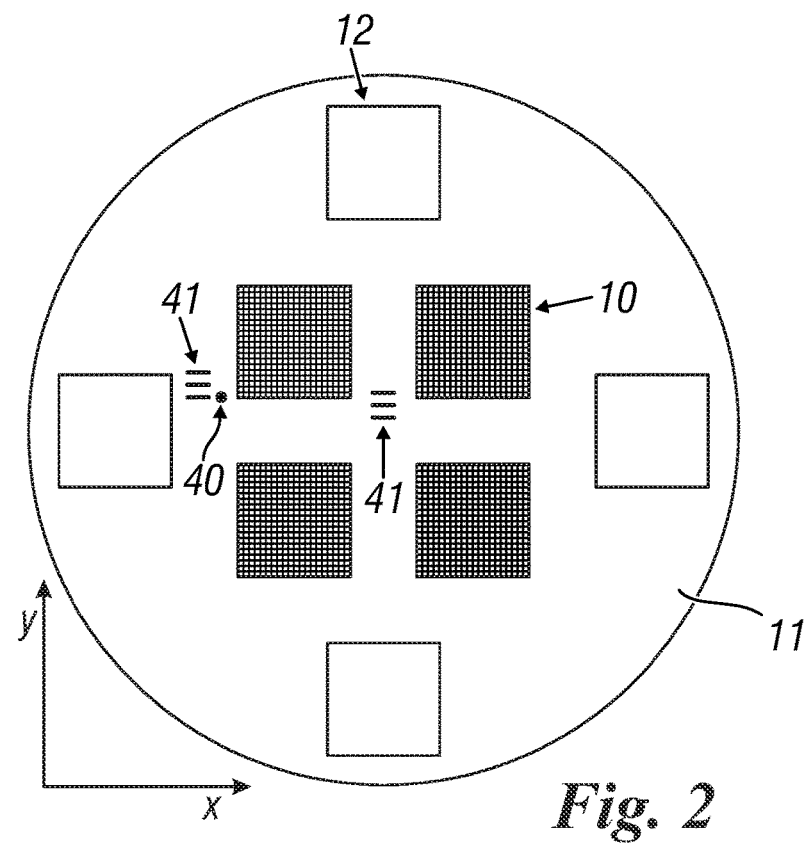
FIG. 2 shows a drawing of an implantable medical device according to the present invention.
Figure 3:
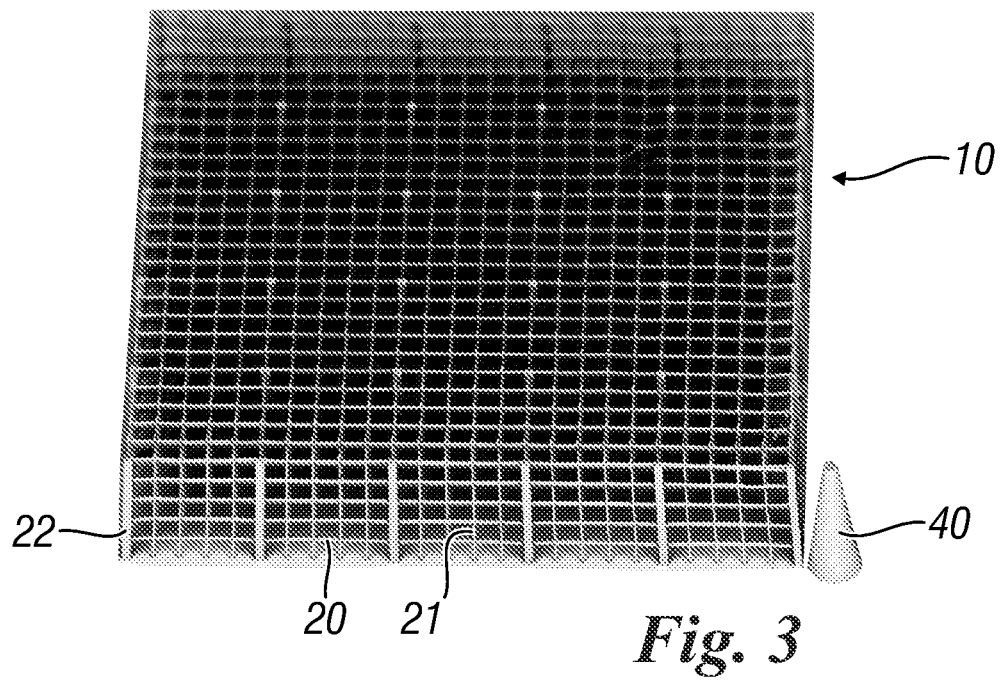
FIG. 3 shows a micrograph of an implantable medical device according to the present invention.
Figure 4:
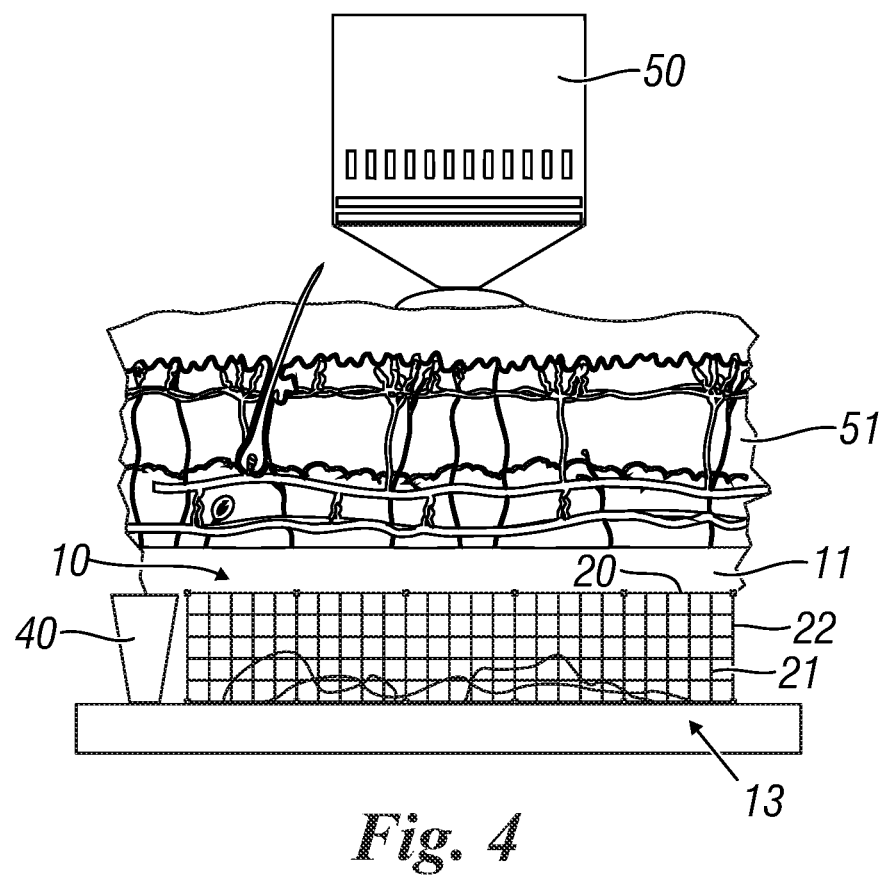
FIG. 4 is a schematic illustration of an implanted medical device inclusive of microscope according to the present invention.
Figure 5:
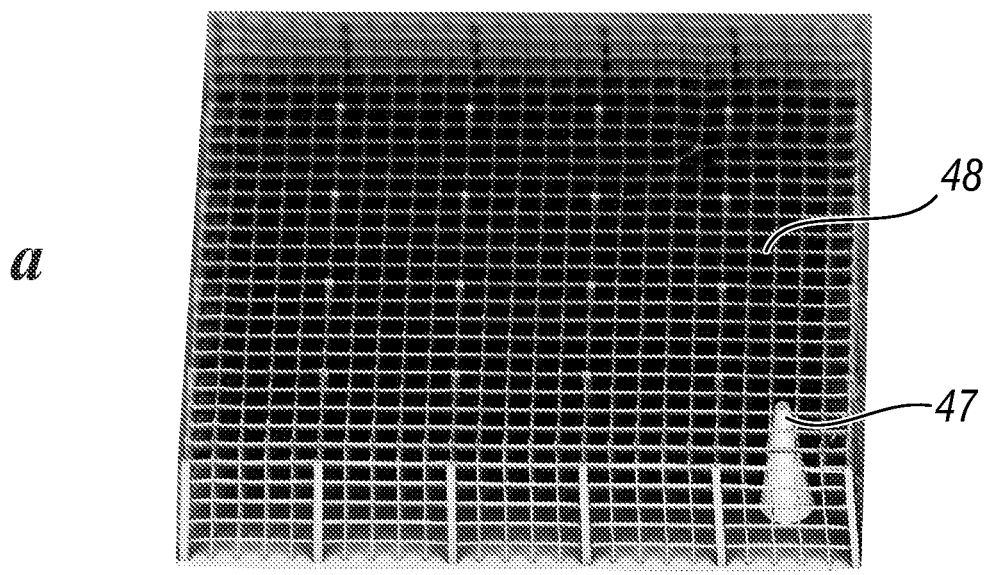
FIG. 5 is a schematic illustration of an implanted medical device, in perspective view (FIG. 5a) and in top plan view (FIG. 5b), which includes a reference element, according to the present invention.
Figure 5:
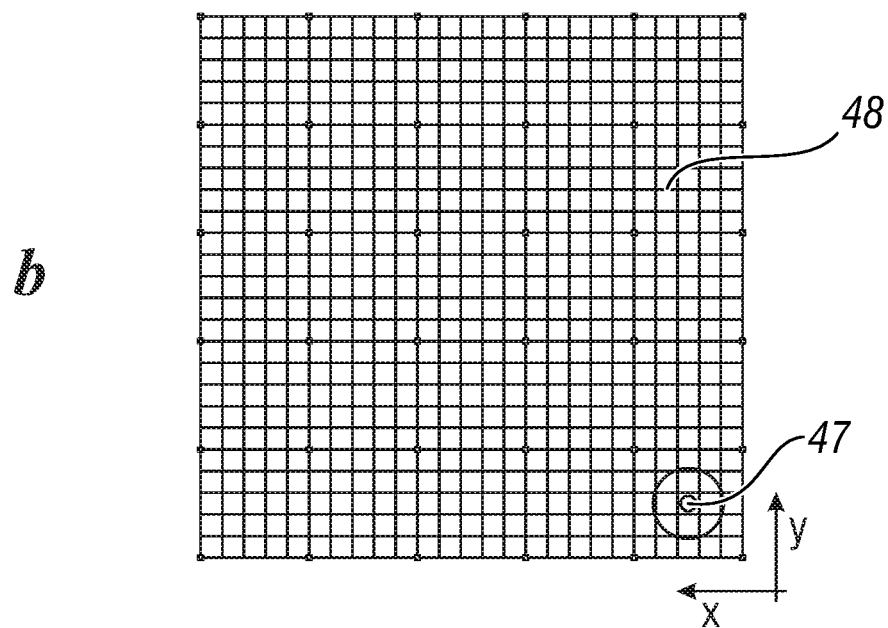

The implantable device is produced using the technique known as two-photon laser polymerisation (2PP). It is carried out via a laser source with a wavelength in the near infrared (NIR) focused in a photosensitive material constituted by a pre-polymer (i.e., monomers and oligomers) and by a photo-initiator.

This phenomenon results in an overall polymerisation of the focal volume, causing in situ cross-linking of the monomers and of the oligomers. The likelihood of two-photon absorption has a quadratic dependence upon the intensity of the IR incident laser beam; consequently, polymerisation occurs only within a volume restricted around the focus. Absorption of two independent and simultaneous photons causes an energy transition that cannot be obtained by absorption of a single infrared photon. Considering the aforesaid non-linear dependence, the polymerised volume obtained is smaller than the focal volume and hence enables a high resolution, of up to 100 nm, thus overcoming the diffraction limit. The devices 10, four of which are illustrated in the figures, have been polymerised on coverslips 11, which have a diameter of 12 mm and/or of 5 mm (150-170 µm, BioOptica, Milan, Italy).

For two-photon polymerisation of the devices 10 an ytterbium femtosecond laser was used, based upon a mode-locking cavity-dumped oscillator with an emission wavelength ranging in the near infrared.

The characteristic wavelength of the laser was 1030 nm, the pulse duration was approximately 300 fs, the repetition frequency was 1 MHz, the maximum pulse energy was 1 µJ, and the maximum average power was 1 W.

As photosensitive material a radical-polymerisation biocompatible hybrid resin known as SZ2080 was used, constituted by a pre-polymer and by a photo-initiator known as IRG (Irgacure 369,2-benzyl-2-(d imethylamino)-1-(4-(morpholinylphenyl)-1-butanone), which is not cytotoxic and is slightly fluorescent. Another possible photo-initiator is BIS (4-4'bis(diethylamino)benzophenone), which is more fluorescent than the previous photo-initiator.

SZ2080 is an inorganic-organic hybrid, the main components of which are methacryloxypropyltrimethoxysilane (MAPTMS), zirconium propoxide (ZPO) and 1% of the IRG photo-initiator. The SZ2080 photoresist presents many advantages, such as biocompatibility, long-term stability, chemical and electrochemical inertia, good optical transmission, and good mechanical stability after polymerisation, and entails a negligible distortion and reduction of the structure during development when compared to other commercially available photoresists.

This resin was deposited by drop-casting on coverslips, in a controlled amount: 30-40 µL for each 12-mm coverslip and 2 µL for each 5-mm coverslip, which subsequently were subjected to a step of baking at 105° C. for 60 min.

At this point, each sample was micro-structured via direct exposure to a focused laser beam.

Slides were used, which enable translation of the sample, mounted on a sample-carrier fixed with respect to the movement system in the three spatial dimensions, thus enabling writing of complex geometries in the resin.

The commands for movement were issued via G-code software, a language commonly used in numeric-control machine tools.

In an embodiment provided by way of example, the software program was written so as to fill, first with all the columns, the circular surface set in the parameters; then, all the gratings in the various planes were formed, first in one direction and then in the other; lastly, reinforced columns (pillars) were obtained, designed to bestow greater stability upon the entire micro-grid.

Finally, the non-irradiated portions of resin were removed by means of a specific alcohol-based developing solution (50% (v/v) 3-pentanone, 50% (v/v) iso-propyl alcohol, Sigma-Aldrich, USA).

Each device 10, in a preferred embodiment, had a shape constituted by a matrix of thin vertical lines 20 (columns) interlaced with various thin horizontal lines 21 (X, Y), thus constituting a number of levels and determining a sequence of cubic pores. These cubic pores, each of which had a side of 20 µm, were positioned alongside each other to form a resulting square structure with a total side of 500 µm. The vertical levels were five in number, and the consequent total height was 100 µm. These dimensions could be varied according to the need.

Preferably, every four columns 21 there is a column having a diameter two to ten times larger than that of the other columns to form a pillar 22.

The pillars 22 are the strongest elementary structure in the entire device. They play a supporting role for the device and issue a significant fluorescent signal in two-photon excitation fluorescence (TPEF) optical microscopy, thus facilitating the focusing operation and possibly correction of any image aberration due to the optical system of the microscope used for observation and to the distortion of the beam by the biological tissue.

Then, in one embodiment of the present invention, set in four end portions of the support 11 are four spacers 12 (having a side of 500 μm and a height of 100 μm, and in any case a height equal to the height of the device 10), which perform a function of structural support for a possible biomaterial 13, which will be positioned above it.

Spatial repositioning in order to be able to view each time the exact point of interest, which must be made at each observation time window, was ensured by appropriately polymerised specific reference points.

In particular, at least one truncated cone 40 was polymerised alongside a device 10. The idea behind this was to provide information on the spatial positioning along the vertical co-ordinate of penetration (Z).

The truncated cone 40 is a reference device, which defines the height focused in the analysis by means of the two-photon excitation fluorescence (TPEF) microscope, or more in general the multi-photon excitation fluorescence microscope, and alternatively by means of a confocal microscope. In the implementation step, the diameters of the lower base and upper base were defined so as to obtain a linear dependence between the diameter of the cone, at a given height, and the height from the support 11 or the height from any other reference element.

Consequently, the operator has to measure the dimension (diameter) of the cone in the current focal plane to verify the height of the level observed.

Instead of the cone 40, it is possible to use other three-dimensional figures that have at least one of their sides inclined, or in any case have a variable cross section, which enables a linear dependence, or even a non-linear dependence, to be obtained between a measurable dimension and the height of the level with respect to a reference plane.

If then the cone 40 is positioned in an asymmetrical way with respect to the device 10 it is also possible to define the origin of the axes X and Y, and hence define with a single marker the three co-ordinates of the device 10.

It may for example be envisaged to position the cone 40, in a unique way, alongside one side of the device 10, in the proximity of a corner, and with respect to the corner positioned in a counterclockwise direction (or clockwise direction).

The cone 40 will be located close to a corner that will be the origin of the axes, where the axis Y will be set along the side, alongside which the cone 40 is positioned.

To facilitate spatial recognition of the device, and in particular to determine the axes X and Y, other reference points were provided in the form of identifiable marks; for example, some tracking references 41 were present to enable fast re-positioning of the microscope at different timepoints. In the central part, the focusing lines were polymerised along the positive axis Y to indicate the direction. Hence, the position of the focusing lines close to a device indicates the direction of the axis X. In effect, these lines were always polymerised from the initial position to the final position.

The device thus obtained can be used, once implanted, for observing growth and vascularisation of the tissue via intravital microscopy.

Alternatively, the device can be used for testing reactions to new biomaterials.

With the devices 10 set on the support 11, the biomaterial 13 adheres to the spacers 12.

For this purpose, it is possible to use a monocomponent glue, or else a biocompatible glue that can be polymerised by UV radiation.

Illustrated in the figures are four devices 10 set on a support 11, but according to the need it is possible to install from one device to as many as are desirable or as many as can be installed on the basis of the size of the support itself.

In an alternative embodiment, the device 10 can be employed without the use of a support 11.

This is obtained, as described previously, with the use of a support, but focusing of the femtosecond laser must not be performed in the proximity of the support but starting from a minimum distance from the support so as to polymerise the device 10 within the SZ2080 resin, leaving part of the resin not polymerised between the device 10 and the underlying support. In this way, the device is not constrained to the support 11 but can be picked up, using appropriate means, and implanted directly without the support.

In another embodiment of the present invention, the device may be inclusive of the truncated cone 40; i.e., instead of providing the truncated cone 40 on the support 11 in a particular position, the truncated cone 47 is provided within the grid structure of the device 48 itself.

Positioning of the truncated cone 47, which in itself enables evaluation of positioning along the axis Z, must preferably be asymmetrical with respect to the device 48 in order to be able to identify the origin of the axes X and Y.

A TPEF microscope 50 proves to be the best technique for viewing the device 10, once it has been implanted beneath the epidermis 51, but also multi-photon or confocal microscopes can be used.

Two-photon excitation is a non-linear process correlated to the simultaneous absorption of two photons. The sum of the energies of the two infrared photons (from 690 nm to 1600 nm) is sufficient to produce a molecular transition to an excited electronic state, which brings about fluorescent emission.

Two-photon excitation requires a high-intensity electrical field supplied by femtosecond lasers with a high repetition rate. This light is focused on the excitation point by high numeric-aperture (NA) lenses.

The main advantages of TPEF lie in the depth of penetration, in the high localisation of the excitation volume, and in the technique used for light detection. In fact, unlike in the case of confocal microscopy, the entire sensitive area of the detector is used, and this enables application of TPEF to samples that are dense (to a depth of 300-1000 μm) and turbid.

This process also provides an immediate practical advantage over confocal microscopy since out-of-focus excitation is prevented, thus reducing photo-damage in the out-of-focus plane, maintaining the possibility of having perfectly clear images in the focal plane during scanning along the optical axis.

The images are obtained by two-photon excitation induced by radiation having a wavelength of 800 nm. The images taken at each level (different heights from the base of the device 10) are captured by a computer 52 and analysed and assembled to make up a three-dimensional image.

For each level of the device 10 an image will hence be obtained, from which it is possible to uniquely identify the height, via the cone 40, from a reference plane that may be the device itself or the support 11. The use of reference systems internal to the device that encode for the position of observation renders such positioning independent of possible imperfections in calibration of the scanning system of the two-photon microscope. Moreover, the known regular geometrical structure of the device enables control of the presence of image aberration due to the optics of the microscope and/or to the distortions of the laser beam as a result of propagation in the biological tissue.

The invention claimed is:

1. An implantable medical device obtained by means of two-photon laser polymerisation of a resin to form a three-dimensional matrix, wherein: said three-dimensional matrix comprises a number of levels distributed in height; and said three-dimensional matrix comprises reference means designed to uniquely identify the height of each level from a pre-set reference by means of a multiphoton fluorescence-excitation microscope; said medical device being characterised in that said reference means comprise a solid having a cross section that varies with height.

2. The device according to claim 1, characterised in that said reference means comprise a truncated cone.

3. The device according to claim 2, characterised in that said truncated cone is set in an asymmetrical position with respect to said three-dimensional matrix.

4. The device according to claim 2, characterised in that said truncated cone is set, on a side of said three-dimensional matrix, in the proximity of a corner, and with respect to the corner is positioned in a counterclockwise direction.

5. The device according to claim 1, characterised in that said reference means comprise trackingreferences for defining the axes X and Y.

6. The device according to claim 1, characterised in that said device is constituted by a matrix of columns interlaced to various horizontal thin lines, to constitute said levels and to determine a sequence of cubic pores of controllable and known size.

7. The device according to claim 1, characterised in that said device is set on a support.

8. The device according to claim 7, characterised in that said support comprises a plurality of spacers and in that a biomaterial is fixed to said spacers.

9. The device according to claim 1, characterised in that said device has dimensions of approximately 500 μm×500 μm×100 μm, with cubic pores, which each have a side of 20 μm.

10. A method for enabling identification, in an implantable medical device, of a height referenced to a reference system using a multiphoton fluorescence-excitation microscope, comprising the step of associating with said device reference means designed to uniquely identify the height of each level from a pre-set reference, by means of a dependence between a measurable dimension of said reference means and the height of the level.

* * * * *